US006351713B1

United States Patent
Board et al.

(10) Patent No.: US 6,351,713 B1
(45) Date of Patent: Feb. 26, 2002

(54) DISTRIBUTED STRESS WAVE ANALYSIS SYSTEM

(75) Inventors: David B. Board, Boca Raton; Craig Hughes, Oviedo; Michael Caulfield, Winter Park; Sylvia Andrews, Oviedo, all of FL (US)

(73) Assignee: Swantech, L.L.C., Fort Lauderdale, FL (US)

( * ) Notice: Subject to any disclaimer, the term of this patent is extended or adjusted under 35 U.S.C. 154(b) by 0 days.

(21) Appl. No.: 09/464,018

(22) Filed: Dec. 15, 1999

(51) Int. Cl.[7] .............................................. G06F 19/00
(52) U.S. Cl. ......................................... 702/42; 702/181
(58) Field of Search ............................... 702/42, 34, 35, 702/36, 182, 183, 184, 185, 81, 84, 56, 179; 706/912, 913, 914, 915

(56) References Cited

U.S. PATENT DOCUMENTS

| | | | | |
|---|---|---|---|---|
| 5,210,704 A | * | 5/1993 | Husseiny | 364/551.01 |
| 5,239,468 A | * | 8/1993 | Sewersky et al. | 364/424.03 |
| 5,309,379 A | * | 5/1994 | Rawlings et al. | 364/578 |
| 5,333,240 A | * | 7/1994 | Matsumoto et al. | 395/23 |
| 5,566,092 A | * | 10/1996 | Wang et al. | 364/551.02 |
| 5,602,761 A | * | 2/1997 | Spoerre et al. | 364/554 |
| 5,608,845 A | * | 3/1997 | Ohtsuka et al. | 395/50 |
| 5,852,793 A | * | 12/1998 | Board et al. | 702/56 |
| 5,875,420 A | * | 2/1999 | Piety et al. | 702/182 |
| 5,952,587 A | * | 9/1999 | Rhodes et al. | 73/862.541 |
| 6,076,405 A | * | 6/2000 | Schoess | 73/587 |

OTHER PUBLICATIONS

Xu et al., "An ANS Based Helicopter Transmission Diagnostic System", IEEE, 8/97.*
Yen, "Health Monitoring of Vibration Signatures", IEEE, date unknown.*
Yen et al., "Health Monitoring of Vibration Signatures in Rotorcraft Wings", IEEE, date unknown.*
Marciano et al., "Mechanical System Condition Monitor (MSCM) System Design", IEEE, Aug. 1990.*

* cited by examiner

*Primary Examiner*—Patrick Assouad
(74) *Attorney, Agent, or Firm*—Malin, Haley & DiMaggio, P.A.

(57) ABSTRACT

A distributed stress wave analysis system is disclosed for detecting structure borne sounds cause by friction. The detected information is processed using feature extraction and neural network artificial intelligence software. The system consists of stress wave sensors, interconnect cables, and preferably three modules: (1) distributed processing units, (2) maintenance advisory panel, and (3) laptop computer. A derived stress wave pulse train which is independent of background levels of vibration and audible noise is used to extract signature features, which when processed by neural networks of polynomial equations, characterize the mechanical health of the monitored components. The system includes an adjustable data fusion architecture to optimize indication thresholds, maximize fault detection probability, and minimize false alarms.

47 Claims, 4 Drawing Sheets

DISTRIBUTED STRESS WAVE ANALYSIS SYSTEM

BACKGROUND OF THE INVENTION

1. Field of the Invention

The invention generally relates to mechanical diagnostic systems, and particularly to a distributed stress wave analysis system for detecting structure borne sounds caused by friction.

2. Description of the Prior Art

All diagnostic techniques are selected to detect discrepant components and monitor their rate of degradation up to the end of their useful life. Thus, they are closely related to inherent reliability and to the rate at which components degrade from fault initiation to loss of intended function.

Since diagnostic techniques are often used during scheduled inspections, the aircraft maintenance and inspection concept forms a critical interface with diagnostics. Diagnostics is the "gate" through which basic reliability, failure progression intervals, and the maintenance/inspection concept must interface to produce the availability, safety, and component removal rates for the overall system.

One of the key relationships in the detection of failures is the one between the failure progression interval and the inspection interval. This relationship determines how often the diagnostic technique will have a chance to detect a discrepancy during the progression of a failure. The concept of this relationship, is what has caused frequent inspections on army aircraft, for example, in order to provide maximum probability of detection.

Army helicopters diagnostic techniques are typically optimized to assure minimum accident rate. However, this has been accomplished at the cost of mission reliability (unnecessary aborts) and mean time between removals ("MTBR") (due to incorrect or premature removals). Over the past several decades, many millions of dollars have been spent to improve the inherent reliability and failure progression intervals related to historically significant failure modes. However, in many cases, the major MTBR and mission reliability benefits of a higher mean time between failures ("MTBF") and slower failure progression cannot be realized without some improvement to the diagnostics gate.

There are four basic parameters that define the accuracy and effectiveness of any diagnostic technique. These parameters are defined as follows:

P1—the probability of calling a good part good;

P2—the probability of calling a good part bad (this parameter represents false indications and P2=1−P1);

P3—the probability of calling a bad part good (these are undetected levels of degradation P3=1−P4); and P4—the probability of calling a bad part bad (these are correctly identified degraded parts).

The effectiveness of any diagnostic technique depends upon the detection threshold employed to indicate a degraded condition. For each possible detection threshold, there is an associated set of P1 and P4 effectiveness values. Variations of the detection threshold invariably produce divergent changes in P1 and P4.

The effectiveness parameters P1 and P4 are also related to the number of times that a diagnostic technique is used during the progression of a fault from "initial discrepancy" to "end of useful life". The more often the test is made, the better the chance of detecting the failure process. While the "instantaneous" probability of detecting a fault is a function of the detection threshold, the "cumulative" probability is a function of the technique utilization interval and the rate of failure progression. The following equation defines how instantaneous probabilities convert to cumulative probabilities of fault detection.

$$P_{4c} = 1-(1-P_{4d})^n \qquad \text{Equation A}$$

Where:

$P_{4c}$=The cumulative probability of detection after "n" uses of the diagnostic technique.

$P_{4d}$=The probability of detection after each use of the diagnostic technique (a "decision cycle").

n=The number of times the diagnostic technique is used during the failure progression interval.

The MTBR and diagnostic technique cost effectiveness are inseparable elements in setting the indication thresholds for any current or proposed technique. Except for the cost savings attributable to accidents prevented by diagnostic/prognostic indications, there is no other area where significant cost savings can be achieved in environments such as the army aviation environment. The MTBR is an expression of the rate at which all component removals occur, regardless of whether or not the removals were justified. Thus, incorrect removals due to false diagnostic indications are a contributing factor to the overall MTBR. Accordingly, it is vital to set indication thresholds that will (a) reliably detect the presence of degradation early in the failure progression interval, and (b) have a very low probability of false indication when used to test healthy components for a period of time that is greater than the component's inherent MTBF. This same type of analysis also applies to the mean time between precautionary landings, mission aborts, and maintenance actions for diagnostic techniques and indications that result in these events.

It is to the effective resolution to achieve these accurate indications that the present invention is directed.

SUMMARY OF THE INVENTION

The present invention provides a distributed stress wave analysis system for detecting structure borne sounds cause by friction. The detected information is processed using feature extraction and polynomial network artificial intelligence software. The system consists of stress wave sensors, interconnect cables, and preferably three modules: (1) distributed processing units ("DPU"), (2) maintenance advisory panel ("MAP"), and (3) laptop computer ("LTC").

Where the system is applied to helicopter drive train components, the sensors, DPU and MAP can be airborne components, while the LTC can be ground based. The DPU can have a serial interface for integration into an airborne Flight Data Recorder or Health Usage Monitoring System ("HUMS").

The stress wave analysis ("SWAN") portion of the system is a high frequency acoustic sensing and signal conditioning technology that provides a time history of friction and shock events in a machine, such as a helicopter drive train. The SWAN portion of the system is similar to the stress wave analysis described and shown in U.S. Pat. No. 5,852,793, issued to Board et al. (the '793 Patent), the disclosure of which is incorporated herein by reference. A derived stress wave pulse train ("SWPT") is independent of background levels of vibration and audible noise. The SWPT preferably is digitized and used to extract signature features, which when processed by neural networks of polynomial equations, characterize the mechanical health of the monitored components.

The system includes an adjustable data fusion architecture to optimize indication thresholds, maximize fault detection probability, and minimize false alarms. System testing preferably indicates a 100% probability of detecting gear or bearing damage within one hour of operation with a discrepant condition, and less than a one tenth of one percent chance of a false alarm during 1000 hours of operation with healthy components. In addition, to accurately detecting faults, the software used by the system will locate a fault, isolate its cause to either a gear or bearing source, display the percent degradation, and estimate its remaining useful life.

The application of artificial intelligence techniques for classification of SWPT features advances current technology to achieve accurate, real time, diagnostic capability at all flight power levels. However, it should be recognized that the hardware and operating system software of the present invention are readily adaptable to numerous other mobile and fixed based applications, and all applications are considered within the scope of the invention.

Accordingly, it is an object of the invention to provide a system that performs distributed stress wave analysis on one or more components of a machine or equipment.

It is another object of the invention to provide a system for reliably detecting the presence of degradation of a component early in the failure progression interval.

It is another object of the invention to provide a system that has a very low probability of false indication when used to test healthy components for a period of time that is greater than the component's inherent mean time between failure.

It is still another object of the invention to provide a system that estimates the remaining useful life of a degraded component.

It is yet another object of the invention to minimize downtime of equipment and machines.

In accordance with these and other objects which will become apparent hereinafter, the instant invention will now be described with particular reference to the accompanying drawings.

DESCRIPTION OF THE PREFERRED EMBODIMENTS

Figure 1:
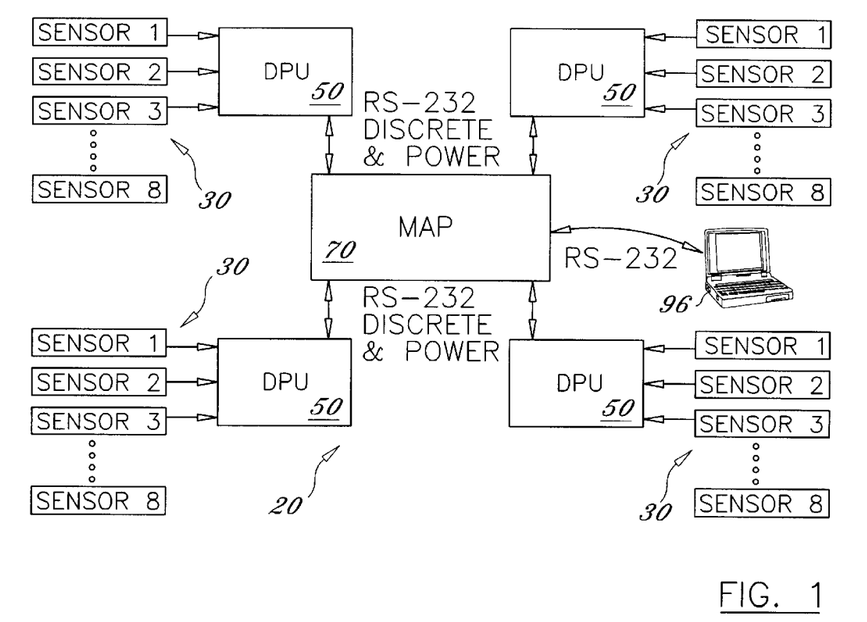
FIG. 1 is a block diagram of the Distributed Stress Wave Analysis system of the present invention.

As seen in FIG. 1 the overall system of the present invention is illustrated and generally designated distributed stress wave analysis system ("DSWAN") 20. System 20 generally consists of one or more, and preferably a plurality of, stress wave sensors 30, interconnect cables and three types of modules: (distributed processing units ("DPU") 50, a maintenance advisory panel ("MAP") 70, and a laptop computer ("LTC") 96, such as, though not limited to, a conventional laptop computer having a PENTIUM or higher processor and preferably running WINDOWS 95 or higher. However, it should be understood that system 20 is not limited to used with PENTIUM processors and WINDOWS operating software, and other microprocessors and operating software can be used with the present invention and all are considered within the scope of the present invention. Sensor cables are used to connect DPU 50 to sensors 30, whereas serial communications and power cables connect DPU 50s to MAP 70. A MAP input cable can also be provided for routing equipment power (i.e. 28V DC aircraft power) to MAP 70 for distribution to DPUs 50.

Preferably, sensors 30, DPUs 50 and MAP 70 are airborne components of system 20 and LTC 96 is ground based, when system 20 is used in conjunction with helicopter drive train components. However, system 20 can be used in many other mobile and fixed based applications, including, but not limited to, diagnosing the condition of gears and bearings in numerous types of mechanical drive trains such as radar components, shipboard machinery and main propulsion equipment, and automotive and helicopter transmissions. Individual DPUs 50 can also be directly interfaced with other mobile and/or fixed based computers through a suitable communications bus.

Preferably, each DPU 50 scans up to eight (8) sensor 30 locations, extracts the friction and shock signal from broadband noise, and uses Anomaly Detection Network ("ADN") 52 software to detect abnormal friction/shock signatures from the monitored components. The eighth sensor 30 can have a dual function of (1) monitoring an associated component and (2) being used by the self-testing software to test and calibrate the associated DPU 50. Each DPU 50 also contains Diagnostic and Prognostic Network ("DPN") software for Sensor Validation Networks ("SVN") 54, Regime Recognition Networks ("RRN") 56 and a self-test. When a potential problem is detected by a DPU 50, an associated indicator is turned "ON" on MAP 70. LTC 96 can be used, during a post flight inspection, to download, analyze, and display, detected and forecasted problems. LTC 96 can also be used to upload new or additional software to the memory of DPU 50, or to reprogram DPU 50 for use with a different set of sensors 30.

In one embodiment, each DPU 50 preferably consists of four (4) circuit card assemblies ("CCA") and two (2) flexible printed circuits ("FPC") contained within an enclosure having two (2) external input/output (I/O) connectors preferably mounted on one side. The four CCAs preferably consist of a Digital Signal Processing ("DSP") module, a Serial Communications and Peripheral Device Control ("SIO") module, a Sensor Interface and Signal Conditioning ("SIF") module, and a Power Supply ("PS") module.

The DSP module is used as DPU 50's system controller and processes the digitized sensor 30 signals. The DSP module, through its central processing unit ("CPU"), communicates with the peripheral resources of DPU 50.

The SIO module can be used as (1) a DPU 50's internal resource communications interface control, (2) a DPU 50's external serial communications interface control, (3) a fault detection discrete external interface. The SIO module can also be used for (1) analog to digital conversion, (2) digital to analog conversion, (3) battery backed-up memory, (4) power distribution and (5) temperature monitoring. The SIO module preferably contains the peripheral interface control logic, which enables the CPU to communicate with all of the resources within DPU 50. These resources include (1)

control and status registers, (2) serial communications controller ("SCC") (which supports both synchronous and asynchronous protocols), (3) temperature sensors, (4) battery backed SRAM, (5) analog to digital converter ("ADC") which converts the conditioned sensor 30 input signal to a digital code for processing by the CPU, (6) digital to analog converter ("DAC") for converting digital code to an analog signal and is used to generate a waveform to test the signal conditioning electronics and the path of each sensor 30 input, and (7) input and output discretes.

Power supply voltages are routed to the ADC to enable power supply monitoring. The SRAM is preferably capable of retaining its data at supply voltages of two volts and with very little current. The SRAM preferably is switched to battery power when main power is not applied and provides nonvolatile storage for stress wave energy data in the absence of power from system 20.

Optically isolated discretes provide an external interface that can be used to set and reset a fault indicator on MAP 70. A re-programmable device can be provided for controlling the logic functions located on the SIO module. The SIO module distributes power to the DSP module and to the SIF module, preferably through mating connectors.

The SIF module is used for sensor constant current drive and multiplexing interface, sensor input signal conditioning, signal conditioning electronics calibration, analog to digital converter input signal multiplexing, emulator interface, programmable integrated circuit programming interface, and temperature monitoring and also includes digital potentiometers. The SIF module provides constant current drive, input buffering, and input multiplexing circuitry to support a plurality of sensor channels, such as eight channels. The SIF module also provides analog signal filtering circuitry for separating stress wave signals detected by sensors 30 from broadband background noise and vibration.

The analog signal filtering circuitry also demodulates the high frequency stress wave signal to a low frequency stress wave pulse train. The stress wave pulse train is then digitized for analysis by the DPN software. The SIF module also provides input multiplexing to the ADC, as well as the de-multiplexing used to steer the DAC output (for testing purposes) to each of sensor 30 inputs.

The SIF module provides a digital temperature sensor, analog torque signal input, and analog discrete input having a programmable trigger threshold, and an input for allowing recorded stress wave pulse train data to be injected into DPU 50 for analysis. SIF module can also provide attachment points and signal buffering for the emulator of the system and the interface used for programming the re-programmable device on the SIO module.

In one embodiment, constant current is generated by sensor 30 input circuitry provided by a current regulator diode forward biased by preferably twenty-four volts DC. Sensor 30 inputs can be buffered, multiplexed to a single output, high pass filtered to eliminate DC offset, and then fed through signal conditioning electronics. The signal conditioning electronic section of the SIF module can include digitally controlled programmable gain stages, a digitally controlled clock tunable bandpass stage, a demodulation stage and a digitally controlled clock tunable lowpass filter stage. The output of the SIF electronic section, and possible other points of the section, are preferably fed to the input multiplexer of the ADC. A test signal, obtained from the DAC, can be injected into the sensor 30-input buffer to test, as well as calibrate, the circuitry.

The PS module can be used for input power conversion for DPU 50's electronics usage, real time clock, battery (i.e. rechargeable NiCad) for battery backed-up memory, integrated battery charger, and temperature monitoring. In the absence of power, the battery keeps the real time clock running and retains data in the battery backed-up memory located on the SIO module. The PS module can include a plurality of DC to DC power converters. Preferably, the real time clock is provided with an integrated trickle battery charger.

MAP 70 can preferably be a communications panel for interfacing the DPUs 50 of system 20, via conventional serial RS-232 communication lines. MAP 70 can fuse and distribute voltage to DPU(s) 50. MAP 70 preferably has one indicator for each DPU 50, which gives a visual indication of detected faults. In one embodiment, MAP 70 accepts power from the monitored equipment (i.e. aircraft) and distributes it to the individual DPU 50s. MAP 70 can have a plurality of indicators, such as four, each under the control of a different DPU 50. The indicators can be magnetically latched and maintain their state until instructed to reset. The indicators preferably provide a visible alert of the detection of an anomalous condition by a DPU 50.

The software used by DPU 50 serves three basic operations: (1) perform self-test (a) power on—comprehensive self-test can be performed, and (b) normal operations—confidence self-test which can run periodically; (2) serial communications routines—communicate to LTC 96 and debug ports, and allow a user to transfer data, reconfigure DPU 50, and control the operation of DPU 50; and (3) sensor 30 tests—contains all necessary functions to process sensor 30 inputs and determine the health of the monitored components.

DPU 50's software preferably consists of an infinite loop, where sensor 30 testing is initiated on boot-up or by command. The software evaluates sensor 30 inputs to determine if the equipment (i.e. aircraft) is operational. The equipment can be considered operational, where a predetermined amount of sensors 30's stress wave energy ("SWE") values are above a minimum value preferably corresponding to a minimum load upon which the diagnostic algorithms have been trained. Once such condition is met, the feature and transient capture data can be save in DPU 50's non-volatile buffers.

Preferably the sensor 30's data is saved during every scan cycle, until at least a certain number of scan cycles (i.e. 10) is saved within the buffer. Once the required number of scan cycles have been saved, the sensor feature data can be saved at predetermined minimum intervals (i.e. every twenty seconds).

The digitized time history (transient capture) data is also saved when the processed time domain feature data from any individual sensor's ADN has been determined to be a worst case event. In such event, corresponding data from all other sensors 30 is also saved. Once the buffer is full, the oldest cycle record will be replaced with the newly acquired data.

Preferably, the operating mode of the monitored equipment or machine is considered "In Regime" when conditions are within specified torque range. Multi-Sensor Regime Recognition 56 software is used, based on predetermined amount of sensors 30 indicating operation within the range, to indicate that the overall system torque is considered to be within the operating regime. When "In Regime" sensors 30 are checked preferably each time they are scanned using one of SVNs 54. Where a sensor 30 fails to indicate valid a predetermined amount of times (i.e. 8 of 10), it is then considered "Invalid". The sensor 30 can regain a "Valid"

status, where its outcome returns to "normal" as determined by the SVN 54. However, where sensor 30 is deemed "Invalid", any Fault Detection Network ("FDN") 80a that requires its input, will preferably be disabled from processing.

Each sensor 30 has its own network and confidence test 58 to determine if an anomaly has occurred. If any ADN 52 determines an anomaly condition, at least one of MAP 70's indicators is turned on. DPU 50 continues to collect sensor and transient capture data, until a time that the SWE levels fall below the minimum operational limits, or are otherwise commanded to halt or stop. Downloading of the sensor history data and transient capture data from DPU 50's memory is preferably commanded by LTC 96.

Figure 3:
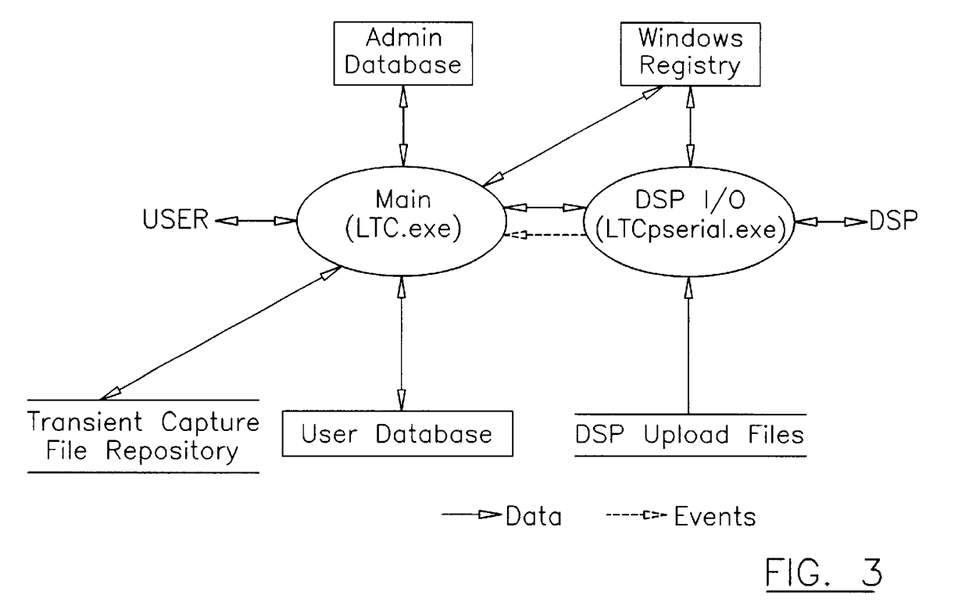
FIG. 3 is a block diagram of certain programs implemented by the laptop computer illustrated in FIG. 1.
Figure 4:
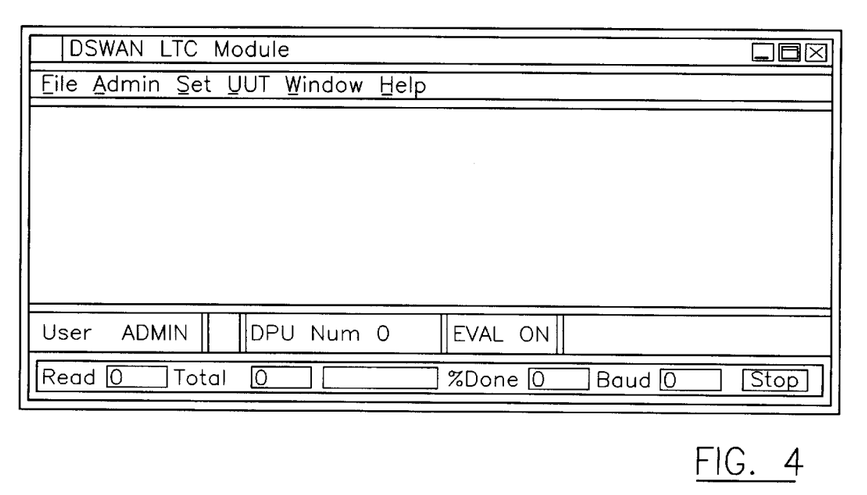
FIG. 4 illustrates the principal user interface screen displayed by the laptop computer illustrated in FIG. 1.

The software used by LTC 96 allows a user to collect data from DPUs 50 and store the collected data in a database for analysis. The SWAN software allows the user to run more detailed analysis of an event, plot trends in the collected data, and create output for reports. LTC 96 serves the following four functions: (1) connect to DPU 50s via MAP 70 serial interface; (2) download data from DPU 50; (3) evaluate certain conditions based on downloaded data; and (4) re-configure DPU 50 by uploading new code and/or arguments. As illustrated in FIG. 3, LTC 96 contains a main program (LTC.exe) and a DSP I/O program (pserialio.exe). The Main Program provides the user interface while the DSP I/O program handles the interface with the DSP module. FIG. 4 illustrates the principal user interface screen, which is displayed by LTC 96.

LTC 96's menu preferably consists of the following items:

| | |
|---|---|
| File | Used to exit the program |
| Admin | |
|    Delete Test Cases | Used to remove collected data |
|    Users | Used to update login information |
| Set | |
|    Identification | Used to identity the test data set |
|    I/O Timeout | Used to set the timeout limit for LTC/DPU communications |
| DPU | |
|    Data | Used to download DPU data |
|    Start/Stop | Used to start/stop the DPU |
|    Reset | Used to reset the DPU |
|    Self-test | Used to initiate DPU self-test |
|    Software | Used to upload new software to the DPU |
|    Time | Used to set the DPU clock |
| UUT | |
|    Evaluate | Used to evaluate UUT health, using saved data |
|    Graphs | Used to plot features of saved data |
| Window | |
|    Tile | Standard windows feature |
|    Cascade | Standard windows feature |
| Help | Used to view version information |

The DPU-Data menu item stops DPU 50 and fetches the DPU Part, DPU Unit Under Test ("UUT"), DPU Status, Elapsed Operating Minutes ("EOM"), ID Prom, Op code, In Regime and Out of Regime data for each sensor 30 that indicates an anomaly failure and, all DPU 50 test records. This data is placed in the database.

The UUT-Evaluate menu item recovers data from the database and evaluates the UUT health as follows: (1) Use Fault Location Network and X of n Confidence Test to validate any indicated sensor anomalies; (2) Choose the validated sensor anomaly with the most extreme data; (3) Use Fault Location networks to evaluate for Port Input Module ("PIM"), Starboard Input Module ("SIM") and/or Main Module ("MM") fault; (4) Use Fault Isolation networks to evaluate Gear and/or Bearing fault; (5) Compute Percent degradation; and (6) Compute Useful life.

Figure 2:
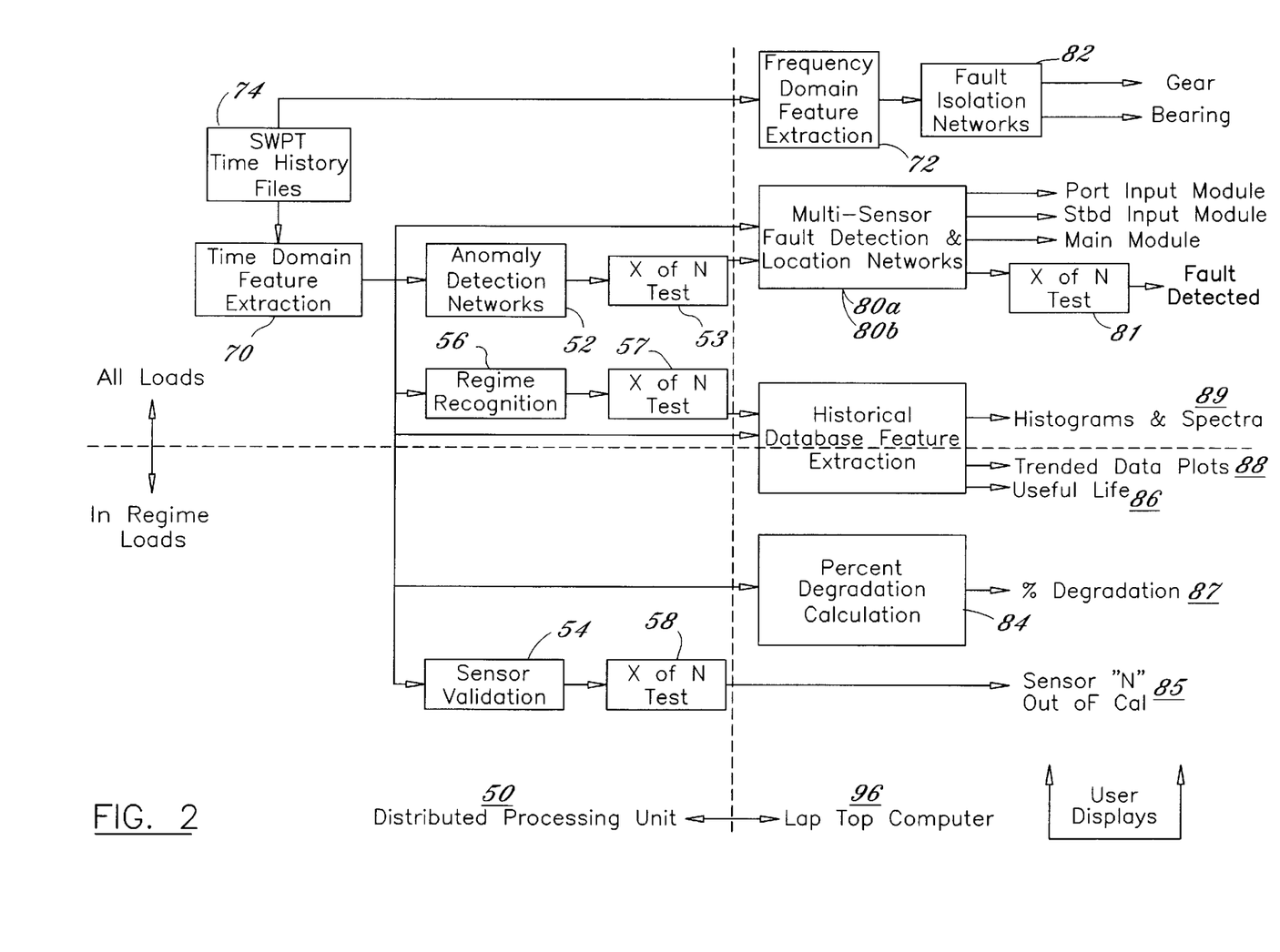
FIG. 2 is a block diagram of the Diagnostic & Prognostic Data Fusion Architecture employed to implement Data Fusion for the Distributed Stress Wave Analysis system of Figure 1.

Feature Extraction ("FE") software is preferably provided for accurately characterizing the SWPT and compressing Time History ("TH") files 74 created from the digitized SWPT data. The FE software can be modular, and can also be used in two versions: (1) Analyst Mode and (2) DPU mode. The Analyst Mode is preferably used in a PC environment for developing input tables for the synthesis and test of the DPNs. The DPU mode preferably provides the operational form of the software, as required by DPU 50 and LTC 96. Preferably, two types of FE are employed (1) Time Domain ("TD") 70 and Frequency Domain ("FD") 72. TD 70 begins with TH file 74 of the SWPT. Mathematical transforms are preferably applied to the time series data for characterization of various waveform features including pulse amplitude, duration and energy content. FD 72 analyzes the waveform preferably using Fourier transform techniques and provides, through a spectrum analysis subroutine, an output of signal amplitude as a function of frequency.

Figure 5:
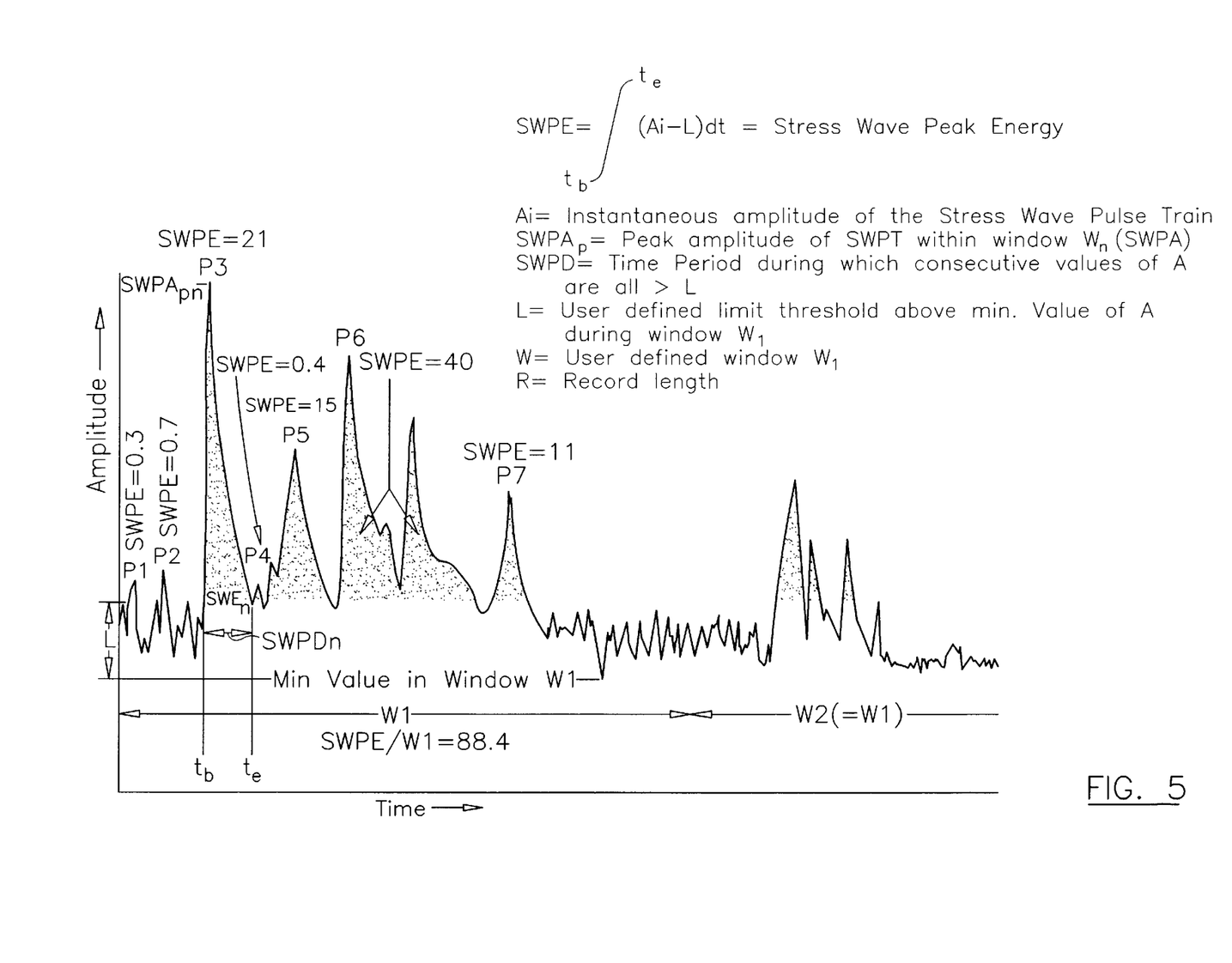
FIG. 5 illustrates a portion of a Stress Wave Pulse Train Time History file.
Figure 6:
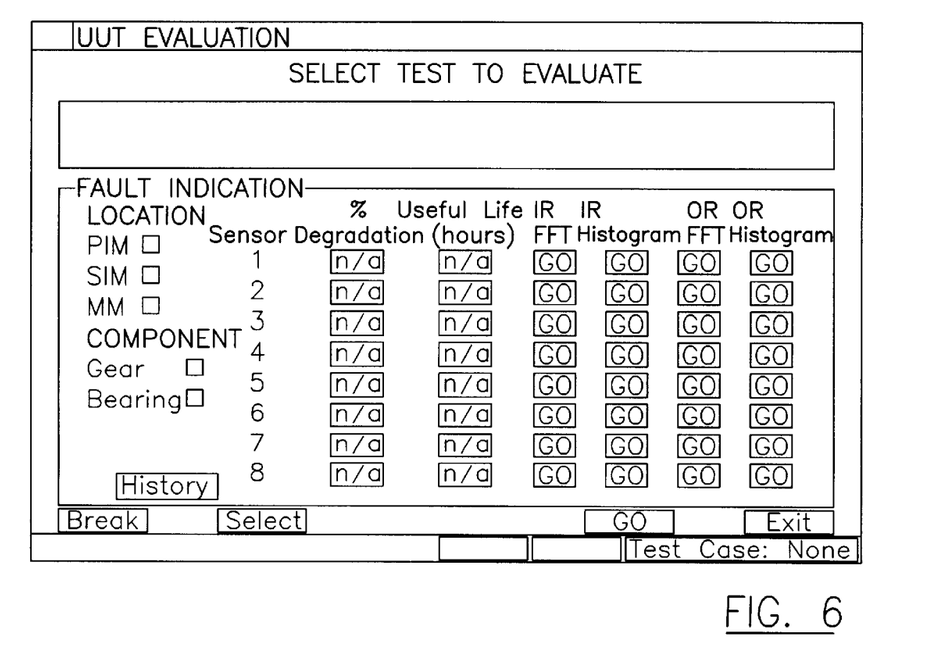
FIG. 6 illustrates a user "Evaluation Form" for use with the present invention.

Thus, FE 70 extracts TD features from SWPT data files. The TDFE 70 software preferably compresses the data into the various waveform features. As seen in FIG. 5, a portion of a SWPT TH file 74 is illustrated. Window ("W") is preferably a user-defined number of milliseconds (typically selected as the period corresponding to a characteristic machine frequency). W's length is preferably constant for the full data record. A data record length ("R") is the total time duration represented by the data file.

Preferably, all but two of the features extracted from SWPT 74 depend upon exceeding a limit threshold "L". This limit L is calculated for each window preferably as a multiple of the mean of the lowest 10% of positive values of the instantaneous amplitude "$A_i$" of the SWPT during the window. The Limit Threshold Factor (LTF) for computing L is constant for the full record length and can be set by the analyst. The LTF preferably affects thirty-five (35) out of thirty-seven (37) time domain features and is used to calculate a threshold that determines when the SWPT signal is "peaking" v. at a background level. A default value for LTF in DPU 50's TDFE 70 software can be provided, such as the value five (5).

The following represents definitions for items appearing in FIG. 5 and features calculated from SWPT time history file 74:

(a) Stress Wave Peak Duration (SWPD)—The period of time between an upward breech of the threshold L and when the $A_i$ next falls below L;

(b) Stress Wave Peak Amplitude (SWPA)—The maximum value of $A_i$, during the SWPD;

(c) Stress Wave Peak Energy (SWPE)—The sum of ($A_i$-L) for each data point during the SWPD;

(d) Stress Wave Peak Energy per Window (SWPE/W)—The sum of all the individual SWPE values within a window;

(e) Stress Wave Energy per Window (SWE/W)—The numeric sum of all the $A_i$ values greater than zero for all data points that occur during all windows of a data record;

(f) Peak Energy Factor per Window (PEF/W)—The ratio of the SWPE/W to the SWE/W;

(g) Stress Wave Energy per Record (SWE/R)—The numeric sum of all the $A_i$ values greater than zero for all data points that occur during all windows of a data record;

(h) Stress Wave Peak Energy per Record (SWPE/R)—The sum of all the individual SWPE values within a record;

(i) Peak Energy Factor per Record (PEF/R)—The ratio of the SWPE/R to the SWE/R;
(j) Peaks per Record (PEAKS/R)—The total number of SWPT peaks that occur during a record; and
(k) Stress Wave Peak Amplitude per Record (SWPA/R)— The maximum $A_i$ value during the record.

Four Statistical Parameters (S1, S2, S3 and S4) can also be calculated for each of the 5 Window Length features, for the full record. These same 4 statistical parameters (describing Probability Density Distributions of the extracted features) are calculated for all the individual SWPA values in the record. This preferably yields 37 time domain statistical parameters of the SWPT. Statistical Parameters (S1, S2, S3 and S4) are defined as follows:

(1) S1—3rd moment test for Normal Distribution; (2) S2—Maximum value of the population; (3) S3—The ratio of (Maximum−Mean)/(Maximum−Minimum); and (4) S4—Ratio of the standard deviation of the population to the mean of the population.

The Analyst Mode version of the FE software preferably formats the 37 time domain features into a spreadsheet that accurately characterizes the SWPT in the Time Domain. The DPU Mode of the FE software, stores the extracted features, preferably as a block of 32 bit integer words, suitable for processing by the DPN's stored in DPU 50's memory, and for download to LTC 96's Ground Station.

Frequency Domain Feature Extraction ("FDFE") 72 begins with SWPT TH file 74 being processed by an FFT spectrum analysis module. Stress Wave Spectral Density ("SWSD") spectra are obtained by RMS averaging, preferably, ten (10) individual time records with 60% overlap of data. Each SWSD can be converted to a table, which identifies the signal amplitude within a predetermined amount of frequency lines. The provided spectral range contains all of the fundamental defect frequencies for the monitored equipment. The frequency lines are then grouped into bands (i.e. 65 bands of 20 lines—50 Hz), and the average amplitude for all 1300 lines, and the maximum amplitude in each band, are preferably calculated. The ratio of the maximum in each band to the 1300 line average is calculated and tabulated as "peak to average" ratios for each band. FDFE 72's software next computes the ratio of the maximum amplitude in all 1300 lines to the average of all 1300 lines. Lastly, the standard deviation can be calculated for the "peak to average" ratios for the bands. The "peak to average" ratios, the 1300 line amplitude magnitude, the max to average ratio, and the standard deviation of the "peak to average" ration are preferably tabulated as sixty eight features that characterize the SWPT in frequency domain.

System 20 preferably includes six different decision making networks: (1) Anomaly Detection Networks ("ADN") 52; (2) Fault Detection Networks ("FDN") 80a; (3) Fault Location Networks ("FLN") 80b; (4) Fault Isolation Networks ("FIN") 82; (5) Sensor Validation Networks ("SVN") 54; and Regime Recognition Networks ("RRN") 56. These networks preferably consist of polynomial equations, which are implemented as separate software objects.

Features, which accurately characterize the SWPT in both the time and frequency domains, are computed with custom Feature Extraction Software. These computed features are then used as inputs to decision making networks of polynomial equations that detect discrepant conditions and measure their severity. Networks of polynomial equations are used to automatically classify the stress wave data as being representative of either healthy or discrepant mechanical components. Numeric modeling software is used to synthesize and evaluate Diagnostic Networks, which use a set of "features" extracted from the SWPT as inputs.

As seen in FIG. 2, the architecture of how the different diagnostic and prognostic networks relate to each other in system 20 is illustrated. The starting point for each of the networks is a digitized time history file 74 of the SWPT signal that is the output of DPU 50's analog signal conditioner ("ASC"). File 74 is processed by Time Domain Feature Extraction ("TDFE") software module 70 to compress the data. In one embodiment, file 74 represents approximately 80 k bytes (based on a 2 second 20 KHz capture), which is compressed by TDFE module 70 to approximately 2.64 K bytes of information. However, it should be understood that the amounts of information that can be contained by file 74 and other ratios of compression can be performed by TDFE module 70, and all are considered within the scope of the invention.

The ASC and operating system of DPU 50 monitor corresponding sensors 30 for opens and shorts. If a sensor Open or Short is detected, processing is discontinued for algorithms that require input from the faulty sensor 30. Each sensor 30 can be provided with a SVN 54 which is a diagnostic network that detects greater than a certain value, such as 10%, loss of sensitivity by a sensor 30. Where SVN 54 consistently indicates that the sensitivity has dropped by more than the preselected value, system 20 will discontinue processing algorithms that require input from the faulty sensor 30 and a "Sensor "N" Out of Cal" message can be logged for post flight download to LTC 96. The consistency of failure indications from SVN 54 is measured by "X of N Confidence Test" 58.

RRN 56 is programmed to classify or categorize stored data preferably according to whether or not the main rotor torque (or other main equipment Load or Speed Parameter) is within a specific range of values (i.e. 25,000<TQMR>35,000 for main rotor torque). This information is required to assure SVN 54, % Degradation 84, and Remaining Useful Life 86 estimates are based upon a relatively narrower range of reference operating conditions. The broader this reference range, the less accuracy for sensor validation and prognostic indications. RRN 56 uses time domain features from multiple sensors mounted on the monitored equipment. RRN 56 requires persistent indication of operation within the predetermined load range (by applying an X of N confidence test 57) to eliminate transient/transition conditions from being labeled as "In Regime" ("IR"). Only IR labeled data is used for sensor validation 54, trended data plots 88, and prognostic computations of percent degradation 84 and remaining useful life 86.

SVNs 54 are provided to detect the occurrence of a sensor/cable assembly that has degraded by loss of sensitivity. A separate SVN 54 is required for each sensor 30. Each sensor 30's SVN 54 is a multi-sensor network using multiple features from each sensor 30 as inputs. To train SVNs 54 to recognize a low output sensor 30, a Sensor Signal Simulator ("SSS") can be used to generate a SWPT at preferably 90% of "normal" gain for the discrepant sensor location. This low sensitivity signal is then processed by the Time Domain Feature Extraction 70 software to compute baseline features. System 20 can also include OPEN and SHORT detection for sensors 30. Where a sensor OPEN/SHORT condition is detected, DPU 50's software turns on MAP 70 indicator for download and display by LTC 96, and all networks requiring the particular sensor 30's input are disabled, until sensor 30 is returned to normal status.

An ADN 52 is preferably provided for each sensor mounted on the main rotor transmission assembly, or other main component of a piece of equipment or machinery being monitored or analyzed. ADN 52 detects the presence of abnormal friction and shock events in the SWPT time domain signal. ADN 52 provides the first step in detecting and confirming the existence of a discrepant condition. Through X of N confidence test 53, an ADN 52 that consistently indicates the presence of abnormal features in SWPT will trigger an indicator on MAP 70 that indicates a requirement for post flight data download to LTC 96. Thus, when any single sensor 30's ADN 52's output consistently indicates a high probability of abnormal friction and shock events, MAP 70 indicator for that particular DPU 50 trips to indicate the need for further evaluation.

ADN 52 can be trained or programmed based on previous extracted data. In one embodiment, ADN 52 is trained to indicate an output of "0" when the input data is from a "good" (i.e. baseline) assembly, and indicates a "1" when the input data is obtained from a "bad" (i.e. seeded fault case) assembly. ADN 52 can also be trained by incorporating time domain feature sets that are computed by DPU 50 from simulated sensor 30 data.

A Sensor Signal Simulator ("SSS") can perform an inverse transform of demodulated SWPT recorded data (i.e. tape recorded data), to convert it to an amplitude modulated signal (i.e. 38KHz) which represents "raw" unconditioned output from a stress wave sensor 30. The raw signal is conditioned (amplified, band pass filtered, and demodulated) by DPU 50, which also computes and stores its time domain features. The time domain features preferably include variations due to different "time slices" for each two-second record. The simulated data also contains variability due to analog conditioning circuits within DPU 50. Preferably, these variables are incorporated into the training of ADN 52 to improve their "robustness".

Where data is downloaded as a result of an ADN 52 alarm, all time domain features from the memory of DPU 50 are transferred to a database located within LTC 96. The features include data from the last "N" measurements on each of sensors 30 connected to corresponding DPU 50, as well as data acquired at predetermined intervals, such as five minutes, for a predetermined period of time, such as fourteen hours of operational monitoring. "N" represents the number of measurements to complete "X of N" confidence test 81 for FDN 80a. The value of "N" is not required to be the same for tests 58, 57, 53 and 81 associated with SVN 54, RRN 56, ADN 52 and FDN 80a, respectively.

Individual sensor ADN 52 alone cannot provide a fault alarm. Rather, ADN 52 alarms trigger a requirement for a DPU 50 download to LTC 96 where the multi-sensor FDN 80a algorithm performs additional analysis to confirm or reject the indication received from ADN 52.

FDN 80a uses the time domain features from multiple sensors 30 to confirm the existence of a fault. FDN 80a runs only after at least one ADN 52 has detected anomalous readings from one or more of sensors 30 monitoring an assembly. When the algorithm of FDN 80a indicates the presence of a discrepant condition, for at least X of N measurement cycles, based upon time domain features from all relevant sensors 30 scanned during a measurement cycle, a fault is considered confirmed and an alarm is displayed on LTC 96.

The selected decision cycle (d) is the amount of time required to complete the measurement and process data for making a pass/fail decision of X of N confidence test 53 that is applied to successive outputs of each sensor 30's ADN 52. The probability of calling a bad part bad at the end of a decision cycle (P4d) is a function of the P4 associated with each measurement ("P4m"), and with the values of X and N for ADN confidence test 53. The value of P4m is in turn a function of the ADN Decision Threshold which is determined by analysis of a "False Alarm, False Dismissal by Threshold" ("FAD") report associated with ADN 52 for each sensor 30.

The FAD report can list the number of correct alarms, correct dismissals, false alarms, and false dismissals, preferably in a database, of examples used to test the accuracy of ADN 52. Thus, with this information, P4m, the probability that an individual ADN 52 processed measurement will call a bad part bad, is calculated as:

$$P4m = \frac{\text{Correct Alarms}}{\text{Correct Alarms} + \text{False Dismissals}} \quad \text{Equation B}$$

Similarly, P2m (the probability that an individual measurement will call a good part bad is calculated as:

$$P2m = \frac{\text{False Alarms}}{\text{Correct Dismissals} + \text{False Alarms}} \quad \text{Equation C}$$

The calculations of P4m and P2m are a function of the evaluation threshold found in the FAD report. This limit is preferably set to minimize the number of false alarms and the number of false dismissals. As these two types of false indications are inversely related, some judgment should be used in selecting an optimum alarm limit ("Decision Threshold"). In making such judgment, the effect of X of N test 53 on P4d and P2d (the probabilities of a valid or false alarm from a decision cycle) is considered, as well as the number of decision cycles during the failure progression interval ("Pi").

The failure progression interval can be defined as the number of operating hours between the time when the fault is detectable (with an accuracy of P4m or better) and the time when further operation is undesirable (due to considerations such as safety, availability, mission capability, economics and/or logistics).

To pass X of N test 53, at least X of N identically performed measurements must exceed ADN 52's Decision Threshold. A binomial distribution can be used to develop the probability of getting a given type of indication upon completion of a decision cycle. Where the probability of each measurement giving a specific type of indication is represented as "Pm" (calling bad part bad—P4m or calling a good part bad—P2m), then the probability of getting that type of indication at the end of a decision cycle is:

$$P_d = \sum_{i=x}^{N} \frac{N!}{X!(N-X)!}(P_m x)(1 - P_m)^{(N-X)} \quad \text{Equation D}$$

This quantity is known as the cumulative term of binomial distribution. Using equations A through D, the cumulative probabilities of false and valid alarms, for different amounts of operating time can be computed and calculated.

Thus, the preferred methodology for optimizing the overall accuracy of system 20 includes the following steps: (1) selecting an indication threshold for individual diagnostic networks (ADNs 52 and FDN 80a) to maximize the ratio of correct indications to false indications, and (2) keep the per measurement probability of false indication low enough to preclude a burdensome frequency of downloading data to LTC 96 for analysis by multi-sensor FDN 80a.

The decision threshold for FDN 80a should be set to yield a 100% probability of finding a bad part during a predetermined amount of time of operational monitoring, such as ten hours, where such the predetermined amount of time is assumed to be less that the failure progression interval. This threshold is considered the minimum P4m requirement for FDN 80a.

The maximum allowable P2m requirement for FDN 80a is driven by what is assumed to be an acceptable probability of having an unjustified component removal or repair, induced by a false alarm, during an assumed period of defect free operation. With certain assumptions, the minimum P4m requirement and the maximum allowable P2m requirement for ADNs 52 can also be calculated.

Thus, FDN 80a analyzes time domain features from multiple sensor locations on an assembly, makes a decision on whether or not there is sufficient evidence to indicate a fault, and implements further analysis if a fault is indicated. Additional analysis routines that can be triggered as a result of a fault indication from FDN 80a include: (1) fault location networks 80b; (2) fault isolation networks 82; and (3) calculation of % degradation 84 and remaining useful life 86.

The time domain feature data downloaded from DPU 50's database consist of the inputs to FDN 80a. This data includes anomalous data sets that resulted in a Decision Threshold exceedance from one or more of sensor 30's ADNs 52, as well as historical data from all sensors 30. The data provides input required for both X of N confidence testing, and for historical trending that is used for remaining useful life projections 86.

Preferably, three FLNs 80b are provided, for a three (3) module assembly, to locate the module that contains component(s) responsible for a Fault Indication/Alarm. Each FLN 80b is trained to locate a fault within one of the three modules of the assembly (where more than three modules are provided, a corresponding number of FLNs 80b will also preferably be provided. FLN 80b use inputs from multiple sensor 30 locations, and are exercised only after test 81 of FDN 80a indicates the existence of a problem. For the example of using system 20 with a helicopter drive train assembly ("helicopter example"), a specific FLN 80b is associated with each of the main rotor transmission assembly modules: (1) Port Input Module ("PIM"), (2) Starboard Input Module ("SIM") and (3) Main Module. A fault condition may or may not result in indications from more than one module.

Each FLN 80b uses time domain features from multiple sensor 30 locations as inputs. As FLN 80b are implemented only after FDN 80a has indicated a fault, they are advisory in nature and cannot, by themselves, cause a maintenance action. Thus, the rationale for setting the decision threshold is to achieve a minimum of 90% probability of correctly locating a fault, while minimizing the probability of a false alarm.

FINs 82 are also exercised only after test 81 of FDN 80a indicates the existence of a problem. Preferably, for the helicopter example, two FINs 82 are provided for each of sensor 30 locations on the main rotor transmission assembly. One FIN 82 is programmed to recognize bearing defects and the other FIN 82 is programmed to identify gear problems. This is done by training FINs 82 to categorize abnormally high amplitude spectral lines as characteristic of either gear or bearing problems. FINs 82 use frequency domain features 72 as inputs and works on the basis of looking for high amplitude spectral lines related to gear and bearing defects. In stress wave analysis, bearing defect frequencies are typically higher than gear defect frequencies. Frequency Domain Feature Extraction 72 is performed by software programmed within LTC 96, using SWPT time history file 74 as an input. Only when required by a DPU 50 ADN 52 alarm, is a time history file 74 for a particular sensor 30 downloaded to LTC 96 for use as the input to Frequency Domain Feature Extraction 72. If more than one sensor 30 ADN 52 is in alarm status, then the file 74 that is downloaded to LTC 96 is chosen by saving the time history only for sensor 30 that has the largest exceedance above its ADN 52 alarm threshold.

All inputs to FINs 82 are from FDFE 72 software. Preferably, both FDFE 72 and FIN 82 software are contained within LTC/ground station software. Preferably, two FINs 82 are provided for each sensor 30, one for the gears and one for the bearings. This allows FINs 82 to identify the presence of multiple causes for a detected defect condition (i.e. when secondary damage occurs) rather than having to choose only one failure mode. As stated above, FIN networks 82 run only after FDN 80a has indicated a fault. Thus, they are advisory in nature and cannot, by themselves, cause a maintenance action. For this reason, the rationale for setting the decision threshold is to achieve a minimum 90% probability of correctly isolating the detected fault to a gear or bearing source, while minimizing the probability of falsely identifying a gear or bearing as the detected defect.

Percent Degradation Calculation ("PDC") 84 is based upon past experience with stress wave analysis of bearing and gear faults for a broad range of high and low speed machines. In the preferred embodiment, PDC 84 assumes that a part is 100% degraded and at the end of its useful life (RED Limit) when its stress wave energy ("SWE") rises to five times its baseline level. The baseline level (at a given sensor 30 location) can preferably be the mean value of IR readings obtained from baseline components. The 0% degradation point (YELLOW limit) is preferably chosen to be the mean plus three times the standard deviation of IR readings obtained from the baseline components. However, it should be understood that other values can be chosen for calculating the RED limit and YELLOW limit and are also considered within the scope of the invention. Thus, in the preferred embodiment the Percent Degradation equation is:

$$\% \text{ Degradation} = \frac{\text{Measured } SWE - \text{YELLOW limit}}{\text{RED Limit} - \text{YELLOW limit}}$$

Preferably, percent degradation 87 is calculated only after test 81 of FDN 80a indicates the existence of a problem. Thus, the Percent (%) Degradation computation 84 uses the Mean and Standard Deviation of the SWE parameter obtained from baseline examples, at each sensor 30 location. The computation is concerned with where the current value of SWE sits, in the region between the Mean plus three Standard Deviations and five times the Means (a conservative Removal Limit). A negative result means that SWE is less than the Mean plus three Standard Deviations. A positive result less than one hundred means that SWE is between the Mean plus three Standard Deviations and five times the Mean. The following calculation can be used:

Degradation=(SWE−(Mean+3*Sigma)/(5*Mean−(Mean+3*Sigma))

Useful Life 86 is calculated using all available data for a Tail Number/DPU preferably up to 10 elapsed operating hours ("EOH") previous to a Fault Indication. The data gives a series of (EOH, SWE) pairs which are used in a linear regression to calculate the approximate slope (m) and x-intercept (b) for the equation $$y=mx+b,$$

where y is SWE and x is EOH

The equation is preferably solved for the expected EOH when SWE is preferably five (5) times the pre-determined mean. The remaining useful life is the difference between the EOH and the current EOH of the system.

DPU 50 stores time domain features for a programmed operational monitoring period, such as approximately fourteen hours in one embodiment, before deleting old data to make room for the new data. Where no anomaly is detected, no data is downloaded from DPU 50 to LTC 96. However, once an anomaly is indicated by DPU 50, it is then downloaded to LTC 96 for further processing. The downloaded data is used by FDN 80*a*, FLN 80*b* and FIN 82. Additionally, sensor(s) 30 responsible for triggering ADN 52 alarms will have their SWPT Time History also downloaded to LTC 96. For these specific sensor(s) 30, an FFT spectrum and amplitude distribution histograms can be plotted 89. The FFT spectrum provides a visual picture of periodic friction/shock event amplitudes and frequencies. The amplitude distribution histogram is a graphic illustration of the lubrication effectiveness and the effects of fluid or particulate lube contamination. "Longer" trended data plots 88 can also be performed and can be useful in evaluating the effect of, or the need for, oil changes and corrective or preventive maintenance actions.

The trended stress wave energy data is preferably used to estimate the remaining useful life 86 of a component. In the preferred embodiment, remaining useful life 86 is estimated by the following:

(1) a linear regression analysis is performed on the last predetermined amount of data points (i.e. 120 data points which could represent ten hours of data) as a function of operating hours;

(2) the time of intersection of the linear function with the "RED" limit is calculated; and (3) the current time is subtracted from the RED limit intersection time, and displayed by LTC 96 as Remaining Useful Life 86.

Only IR data is used in percent degradation calculations 84, trended data plots 88, and remaining useful life estimates 86. The SWPT FFT Spectra and Amplitude Distribution Histograms 89 can be generated from either IR data or Out of Regime ("OR") data.

Summarizing the above, ADNs 52 detect abnormal features in the stress wave pulse train. FDNs 80*a* indicate the presence of damage, including single and multiple faults. FLNs 80*b* identify the assembly modules that contain faulty components. FINs 82 indicate specifically a bearing defect or a gear defect at the location identified by FLN 80*b*. RRN 56 is used for forecasting Remaining Useful Life 86 and % Degradation 87 determinations.

Where the present invention system 20 was used with a helicopter drive train, the monitored components included all of the primary drive train elements except the engines. In this example, fifteen sensor 30 locations were provided which included (1) port input module input housing; (2) port input module output housing; (3) starboard input module input housing; (4) starboard input module output housing; (5) main module planetary ring gear; (6) main module upper cover; (7) tail rotor output/rotor brake support bracket; (8) forward tail rotor shaft support bearing; (9) mid tail rotor shaft support bearing; (10) forward disconnect coupling support bearing; (11) aft disconnect coupling support bearing; (12) intermediate gearbox input; (13) intermediate gearbox output; (14) tail rotor gearbox input; and (15) tail rotor gearbox output.

In use and where five sensors 30 are provided for each DPU 50, for each sensor 30 where DPU 50 indicates a possible anomaly, the following steps are preferably performed by system 20:

(a) In Regime and Out of Regime data is obtained;

(b) The In Regime data is discarded if it indicates that the sensor 30 failed;

(c) The Out of Regime data is discarded if it indicates that the sensor 30 failed;

(d) If both the In Regime data and the Out of Regime data have not been discarded, then the time indicated by the worst of the In Regime data and Out of Regime data is used as a reference time to get preferably ten (10) cycle records including and prior to the reference time;

(e) If not, record indicates that a sensor 30 failed, then run each record through the Fault Detection Network;

(f) If 8 of the 10 records failed the FDN then mark this sensor 30 as a candidate for analysis; and (g) return to (a) for the next sensor 30.

Once all of the sensor 30 candidates have been found from the above steps, the following steps are performed by system 20:

(a) the worst case from all sensor 30 candidates is chosen;

(b) the cycle record from the same time of the chosen sensor 30's worst case data is selected and used for the following:

Run the PIM fault network;
Run the MM fault network;
Run the SIM fault network;
Run GEAR network for sensor 1
Run BEARING network for sensor 1
Run GEAR network for sensor 2
Run BEARING network for sensor 2
Run GEAR network for sensor 3
Run BEARING network for sensor 3
Run GEAR network for sensor 4
Run BEARING network for sensor 4
Run GEAR network for sensor 5
Run BEARING network for sensor 5
Evaluate Percent Degradation based on Sensor 1
Evaluate Percent Degradation based on Sensor 2
Evaluate Percent Degradation based on Sensor 3
Evaluate Percent Degradation based on Sensor 4
Evaluate Percent Degradation based on Sensor 5
Calculate Useful Life based on Sensor 1
Calculate Useful Life based on Sensor 2
Calculate Useful Life based on Sensor 3
Calculate Useful Life based on Sensor 4.
Calculate Useful Life based on Sensor 5.

The instant invention has been shown and described herein in what is considered to be the most practical and preferred embodiment for an example helicopter drive train. It is recognized, however, that departures may be made therefrom within the scope of the invention and that obvious modifications will occur to a person skilled in the art.

What is claimed is:

1. A distributed stress wave analysis system for identifying and analyzing a fault in one or more components of a machine, comprising:

means for detecting a fault in at least one component of a machine, said means for detecting including an anomaly detection network for identifying abnormal features in acquired data followed by the performance of a first X of N confidence test, said means for detecting also including a fault detection network triggered by said anomaly detection network and the first X of N confidence test to confirm or reject a possibly discrepant condition identified by said anomaly detection network, said fault detection network performing a second X of N confidence test for confirming or rejecting the discrepant condition identified by said anomaly detection network;

means for locating the detected fault; and means for isolating a source for the fault.

2. The distributed stress wave analysis system of claim 1 further comprising means for calculating a percent degradation of said at least one component.

3. The distributed stress wave analysis system of claim 2 further comprising means for displaying the calculated percent degradation.

4. The distributed stress wave analysis system of claim 1 further comprising means for estimating a remaining useful life for said at least one component.

5. The distributed stress wave analysis system of claim 1 wherein said first source is a gear source and said second source is a bearing source.

6. The distributed stress wave analysis system of claim 1 wherein said system is implemented with data fusion architecture to process multiple data inputs into reliable and accurate decisions.

7. The distributed stress wave analysis system of claim 6 wherein said data fusion architecture optimizes indication thresholds, maximizes fault detection probability and minimizes false alarms.

8. A method for identifying and analyzing a fault in one or more components of a machine, comprising the following steps:

(a) detecting a fault in at least one component of a machine, said step of detecting a fault including the steps of identifying abnormal features in acquired data by a anomaly detection network followed by the performance of a first X of N confidence test, triggering a fault detection network to confirm or reject a possibly discrepant condition identified by said anomaly detection network and the first X of N confidence test, said fault detection network performing a second X of N confidence test for confirming or rejecting the discrepant condition identified by said anomaly detection network;

(b) locating the detected fault; and (c) isolating a source for the fault.

9. The method of identifying and analyzing a fault of claim 8 further comprising the step of calculating a percent degradation of said at least one component.

10. The method of identifying and analyzing a fault of claim 9 further comprising the step of displaying the calculated percent degradation.

11. The method of identifying and analyzing a fault of claim 9 further comprising the step of estimating a remaining useful life for said at least one component.

12. The method of identifying and analyzing a fault of claim 8 wherein said method employs diagnostic techniques Utilization Interval, Decision Threshold, and an "X of N" Confidence Test, to achieve specified system accuracy in terms of probability of detection and probability of false alarm.

13. The method of identifying and analyzing a fault of claim 8 wherein said method employs an "X of N" Confidence Test, to reduce system sensitivity to transient conditions and reduce probability of false alarm.

14. A distributed stress wave analysis system for identifying and analyzing a fault in one or more components of a machine, comprising:

at least one sensor;

at least one distributed processing unit in communication with said at least sensor, said at least one distributed processing unit extracting shock and friction information received from said at least one sensor, wherein said at least one distributed processing unit performs extraction of feature information relating to time domain and frequency domain characteristics of the shock and friction raw signals received from said at least one sensor and compresses the raw data into extracted feature information;

a maintenance advisory panel in communication with said at least one distributed processing unit, and a computer.

15. The distributed stress wave analysis system of claim 14 wherein said at least one sensor is a plurality of sensor groups and said at least one distributed processing unit is a plurality of distributed processing units, each of said sensor groups in communication with a corresponding one of said plurality of distributed processing units, wherein the plurality of distributed processing units are interfaced to each other by said maintenance advisory panel.

16. The distributed stress wave analysis system of claim 15 wherein said maintenance advisory panel having a visual indicator for each of said plurality of distributed processing units to provide a visual indication of a detected fault by one or more of the distributed processing units.

17. The distributed stress wave analysis system of claim 14 wherein said computer is a laptop computer.

18. The distributed stress wave analysis system of claim 14 wherein said system is implemented with data fusion architecture to process multiple data inputs into reliable and accurate decisions.

19. The distributed stress wave analysis system of claim 18 wherein said data fusion architecture optimizes indication thresholds, maximizes fault detection probability and minimizes false alarms.

20. A method for identifying and analyzing a fault in one or more components of a machine, comprising the following steps:

(a) extracting friction and shock signals from broadband noise received from at least one sensor associated with at least one monitored component of a machine;

(b) detecting abnormal friction/shock signatures from the extracted signal, said step of detecting abnormal friction/shock signatures including the steps of identifying a possibly discrepant condition by an anomaly detection network and performance of a first X of N confidence test, which when passed triggers a fault detection network to confirm or reject the possibly discrepant condition identified by said anomaly detection network and the first X of N confidence test, and confirming or rejecting the discrepant condition identified by said fault detection network by performing a second X of N confident test;

(c) locating a fault causing the detected abnormal friction/shock signature;

(d) isolating a cause of the fault to a gear source or a bearing source.

21. The method of identifying and analyzing a fault of claim 20 further comprising the step of calculating a percent degradation of the at least one component detected to contain the fault.

22. The method of identifying and analyzing a fault of claim 21 further comprising the step of displaying the calculated percent degradation.

23. The method of identifying and analyzing a fault of claim 20 further comprising the step of estimating a remaining useful life for the at least one component detected to contain the fault.

24. The method of identifying and analyzing a fault of claim 20 wherein said method employs diagnostic techniques Utilization Interval, Decision Threshold, and an "X of N" Confidence Test, to achieve specified system accuracy in terms of probability of detection and probability of false alarm.

25. The method of identifying and analyzing a fault of claim 20 wherein said method employs an "X of N" Confidence Test, to reduce system sensitivity to transient conditions and reduce probability of false alarm.

26. The distributed stress wave analysis system of claim 1 wherein said means for locating is triggered only after said fault detection network and the second X of N confidence test confirms the discrepant condition.

27. The distributed stress wave analysis system of claim 1 wherein said means for isolating is triggered only after said fault detection network and the second X of N confidence test confirms the discrepant condition.

28. The method for identifying and analyzing a fault of claim 8 wherein said detected fault it located only after said fault detection network and the second X of N confidence test confirms the discrepant condition.

29. The method for identifying and analyzing a fault of claim 8 wherein the source of the fault is isolated only after said fault detection network and the second X of N confidence test confirms the discrepant condition.

30. The method for identifying and analyzing a fault of claim 20 wherein said detected fault it located only after said fault detection network and the second X of N confidence test confirms the discrepant condition.

31. The method for identifying and analyzing a fault of claim 20 wherein a source of the fault is isolated only after said fault detection network and the second X of N confidence test confirms the discrepant condition.

32. The distributed stress wave analysis system of claim 14 wherein said at least one distributed processing unit is located remote of said computer.

33. A distributed stress wave analysis system for identifying and analyzing a fault in one or more components of a machine, comprising:
  means for detecting a fault in at least one component of a machine, said means for detecting including feature extraction software to intelligently compress a large amount of data acquired from machinery mounted instrumentation into a small amount of information that accurately characterizes the large amount of data, said extracted features serving as inputs to an anomaly detection network for identifying abnormal (anomalous) features in the data acquired from machinery mounted instrumentation, followed by the performance of a first X of N confidence test, said means for detecting also including a fault detection network triggered by said anomaly detection network and its associated X of N confidence test to confirm or reject a possible discrepant condition identified by said anomaly detection network, said fault detection network performing a second X of N confidence test for confirming or rejecting the discrepant condition identified by said anomaly detection network;
  means for locating the detected fault; and
  means for isolating a source for the fault.

34. A method for identifying and analyzing a fault in one or more components of a machine, comprising the following steps:

(a) detecting a fault in at least one component of a machine, said step of detecting a fault including the steps of running feature extraction software to intelligently compress a large amount of data acquired from machinery mounted instrumentation into a small amount of information that accurately characterizes the large amount of data, said extracted features serving as inputs to an anomaly detection network to identify abnormal (anomalous) features in the data acquired from the machinery mounted instrumentation, followed by the performance of a first X of N confidence test, triggering a fault detection network to confirm or reject a possible discrepant condition identified by said anomaly detection network and its associated X of N confidence test, said fault detection network performing a second X of N confidence test for confirming or rejecting the discrepant condition identified by said anomaly detection network;

(b) locating the detected fault; and (c) isolating a source for the fault.

35. The distributed stress wave analysis system of claim 33 wherein said means for locating is triggered only after said fault detection network and the second X of N confidence test confirms the discrepant condition.

36. The distributed stress wave analysis system of claim 33 wherein said means for isolating is triggered only after said fault detection network and the second X of N confidence test confirms the discrepant condition.

37. The method for identifying and analyzing a fault of claim 34 wherein said detected fault it located only after said fault detection network and the second X of N confidence test confirms the discrepant condition.

38. The method for identifying and analyzing a fault of claim 34 wherein the source of the fault is isolated only after said fault detection network and the second X of N confidence test confirms the discrepant condition.

39. The distributed stress wave analysis system of claim 1 wherein said means for detecting including feature extraction software to intelligently compress a large amount of data acquired from machinery mounted instrumentation into a small amount of information that accurately characterizes the raw data, said extracted features serving as inputs to said anomaly detection network.

40. The distributed stress wave analysis system of claim 1 wherein said fault detection network incorporating features extracted from multiple sensors.

41. The distributed stress wave analysis system of claim 33 wherein said fault detection network incorporating features extracted from multiple sensors.

42. The distributed stress wave analysis system of claim 1 wherein said anomaly detection network having one or more classification test each having an output determined by a variable passing through a limit threshold.

43. The distributed stress wave analysis system of claim 42 wherein successive classification test outputs are subjected to the first X of N confidence test requiring that the classification test output remains the same for X out of N measurement and test cycles.

44. The distributed stress wave analysis system of claim 42 wherein a "X" parameter of the first X of N confidence test, a "N" parameter of the first X of N confidence test, and the limit threshold for each limit threshold are adjustable.

45. The distributed stress wave analysis system of claim 33 wherein said anomaly detection network having one or more classification test each having an output determined by a variable passing through a limit threshold.

46. The distributed stress wave analysis system of claim 45 wherein successive classification test outputs are subjected to the first X of N confidence test requiring that the classification test output remains the same for X out of N measurement and test cycles.

47. The distributed stress wave analysis system of claim 45 wherein a "X" parameter of the first X of N confidence test, a "N" parameter of the first X of N confidence test, and the limit threshold for each limit threshold are adjustable.

* * * * *